United States Patent [19]

Bajon et al.

[11] 4,208,675

[45] Jun. 17, 1980

[54] METHOD AND APPARATUS FOR POSITIONING AN OBJECT

[75] Inventors: Jean Bajon; Michel Cattoen; Jacques Douchez, all of Toulouse; Jean-Pierre Morucci, Portet-sur-Garonne, all of France

[73] Assignee: Agence Nationale de Valorisation de la Recherche (A.N.V.A.R.), Neuilly-sur-Seine, France

[21] Appl. No.: 888,558

[22] Filed: Mar. 20, 1978

[51] Int. Cl.² .............................................. H04N 7/18
[52] U.S. Cl. ..................................... 358/93; 358/101; 358/107; 358/183; 358/903
[58] Field of Search ................. 358/107, 93, 101, 183, 358/903

[56] References Cited

U.S. PATENT DOCUMENTS

| | | | |
|---|---|---|---|
| 3,814,845 | 6/1974 | Hurlbrink | 358/101 |
| 3,899,634 | 8/1975 | Montone | 358/101 |
| 3,903,363 | 9/1975 | Montone | 358/101 |
| 3,988,535 | 10/1976 | Hickman | 358/101 |

FOREIGN PATENT DOCUMENTS 2314542  11/1978  France.

Primary Examiner—Howard W. Britton
Attorney, Agent, or Firm—Shlesinger, Arkwright, Garvey & Dinsmore

[57] ABSTRACT

A method and apparatus for positioning an object in space in such a manner as to permit duplication of the positioning in a precise position wherein three characteristic points on the object wherein the coordinates of the points are determined and are electrically synthesized for generation of a signal for reproducing the points on the coordinates, and utilizing a television camera and monitor forming an image of the object on the screen and causing the points of the object to coincide with the reference points by means of a photosensitive sensor in such a manner that the characteristic points on the body are displaced so as to coincide with the synthesized points on the television screen.

10 Claims, 8 Drawing Figures

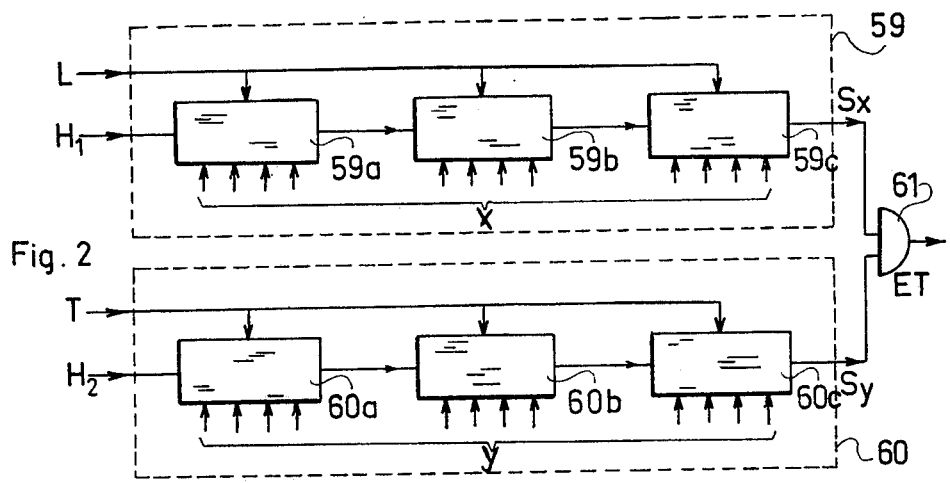
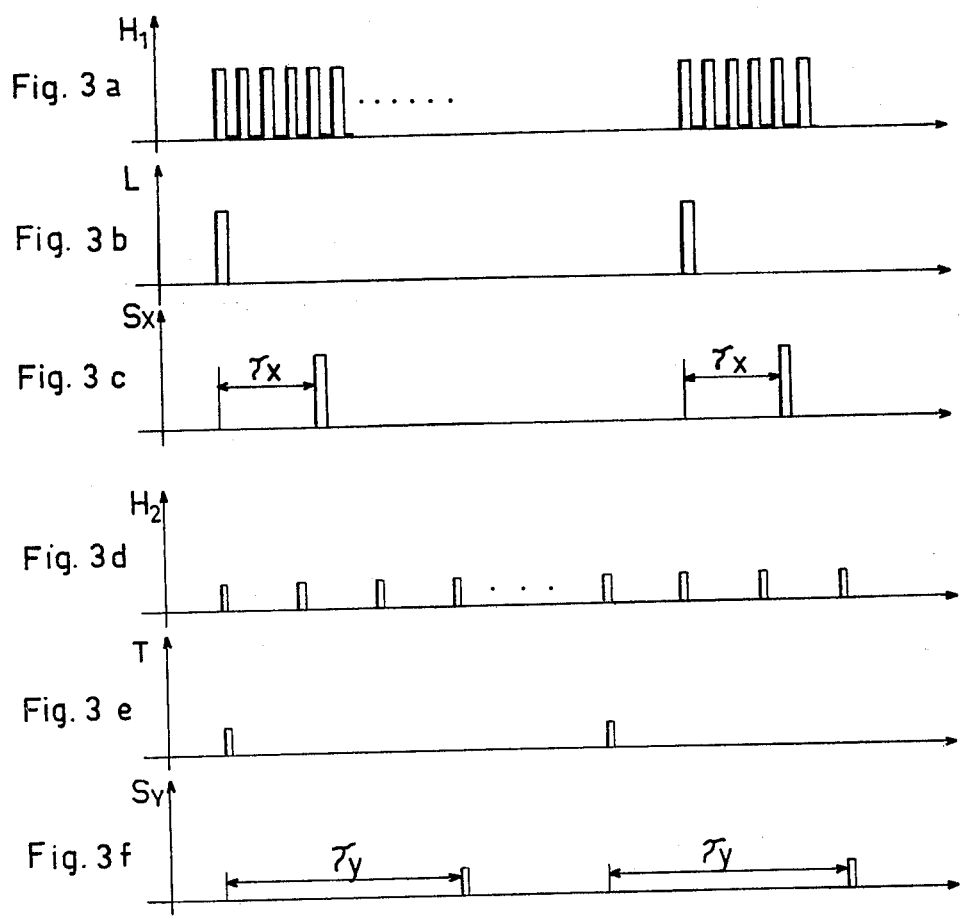

METHOD AND APPARATUS FOR POSITIONING AN OBJECT

This invention relates to a device and a process for positioning an object or a body in space in a fashion which can be reproduced. It is particularly applicable in the medical field, in radiation treatments where it is necessary to replace a sick person in a position identical to the position of the previous session for each treatment. The device which is the object of the present invention permits positioning much more precisely and rapidly than technology in use today such as plastering, laser devices, or other such techniques.

An electronic device which measures and furnishes the coordinates of one or more points from television images has been described in French Pat. No. 75-18561, filed June 13, 1975 and published under U.S. Pat. No. 2,314,542 (Assignee: Agence Nationale de Valorisation de la Recherche A.N.V.A.R.; Inventors: Jean BAJON, Michael CATTOEN, Jean ALQUIER, Henri MAUREL). The present invention proposed an improvement on this device for reproducible positioning of an object or body in space. For this, the invention includes:

a television camera capable of furnishing a video signal of the object;

a television monitor coupled to the camera to visualize the image captured by the camera;

a synchronization clock adapted to furnish visual temporal reference signals, particularly to control the electronic sweep of the camera;

a photosensitive sensor which can be displaced on the screen of the monitor and adapted to deliver a signal characteristic of luminance of the zone opposite which it is placed;

a threshold detector, connected to the photosensitive sensor to receive the signal furnished by the sensor and to deliver an impulse when this signal exceeds a predetermined threshold;

a frame positioning circuit, connected to the threshold detector and to the synchronization clock and being adapted to deliver a control signal at vision frequency, set off in relation to the received impulse so as to center a frame around the zone opposite which is placed the photosensitive sensor;

a frame generator, connected to the aforementioned positioning circuit and furnishing a frame signal which can have two values, the one corresponding to a limited zone, called a frame, the other corresponding to zones beyond the limited zone;

a set-off index circuit, controlled by the frame positioning circuit and delivering a signal which is set off from the signal issuing from the frame positioning circuit in order to position an index at vision frequency outside the frame which is constant relative to the frame;

an index generator, connected to the set-off index circuit and adapted to furnish an index signal characterizing one image point;

a video mixer connected to the camera and the frame generator and the index generator, this mixer's output being connected to the television monitor to furnish it with a video signal representing the image of the aforementioned plane on which are superimposed the frame and the index, and said video mixer is adapted to confer a predetermined luminance to said frame;

a measuring assembly connected to the index generator and to the clock to receive the index generator and the clock reference signals, this assembly being adapted to measure the time separating the arrival of the index signals and the reference signals, said assembly furnishing the signals showing the position of the points coinciding with the index;

a manual control selector having two sets of inputs and one set of outputs and adapted to connect its set of outputs to one of the sets of inputs, according to the condition of its manual control, and one of these sets of inputs is connected to the measuring assembly to receive the signals issued from it;

a storage with capacity to store the coordinates of at least one point, this storage having a set of outputs connected to the other set of inputs of the selector;

a buffer with capacity to store the coordinates of at least one point and having a manual release entry control, this storage being connected with the group of outputs from the selector and being provided with a group of outputs for each point to be stored;

at least one point synthesizer receiving the clock signals and the signals issued from one set of outputs from the buffer, this synthesizer delivering the impulses characterizing the point at vision frequency, and these impulses being received by the VIDEO mixer to be added to the VIDEO signal and to generate at least one luminous zone of small dimensions by superimposition on the screen of the monitor.

The device is adapted to permit acquisition of the coordinates of three points and synthesis of the three corresponding image points simultaneously on the screen of the monitor. For this, it has three synthesizers of points arranged in parallel and connected to three sets of outputs from the buffer; these synthesizers deliver the impulse characterizing each of the points to the VIDEO mixer by means of an or logic function mixer so as to simultaneously apply the image of the three synthesized points to the screen of the monitor.

To position an object or a body in the space, three characteristic points are located on the body, either the formerly marked points (for example tatooed on the skin of a patient), or the particular points of the object of the body which are easily identified (anatomic points of a patient, etc. . . . ).

The device is activated in two phases, first the acquisition of the coordinates of the three identification points when the body or object is found in the position to be reproduced, then the synthesis of three image points to permit a new positioning of the body or the object. The first phase is:

to take aim on the object or the body with camera to form an image of it on the screen of the monitor, to cause the index to coincide with one of the identification points by displacement of the photosensitive marker, to control the entry of the coordinates of the index into the buffer, wherein the selector is in the position which assures the connection between this buffer and the measuring assembly, and to effect the same operations for the two other points and to transfer the coordinates of the three points into the storage.

The second phase consists of controlling the selector to transfer the contents of the storage into the buffer and displacing the object or the body to bring these characteristic points to coincide with the points which are synthesized on the screen of the television monitor.

The storage can be manual loading storage associated with the means of forming the coordinates, adapted to be handled by an operator. These means can be constituted of a keyboard to compose the coordinates in numeric form and to introduce them into the storage in coded form. These means can also be a system of coding wheels which store coordinates and deliver signals characterizing these coordinates at their output.

In another embodiment, the storage is an automatic load storage of which the inputs are connected to the outputs of the buffer to receive the coordinates from the buffer. This arrangement avoids manual transcription of the coordinates. The storage can be constituted of a known magnetic card or perforated card device. In medical application, each patient has a card on which the coordinates of the identification points have been automatically registered in the course of the first treatment. This card is read by a reading head in the course of subsequent treatments to synthesize the image points to permit positioning of the patient.

Other characteristics, objects and advantages of the invention will appear in the following description relative to the attached drawings which show embodiments of the invention.

FIG. 2 shows an embodiment of one sub-assembly of the device.

FIGS. 3a, 3b, 3c, 3d, 3e, 3g are chronograms illustrating the function of this sub-assembly.

Figure 1:
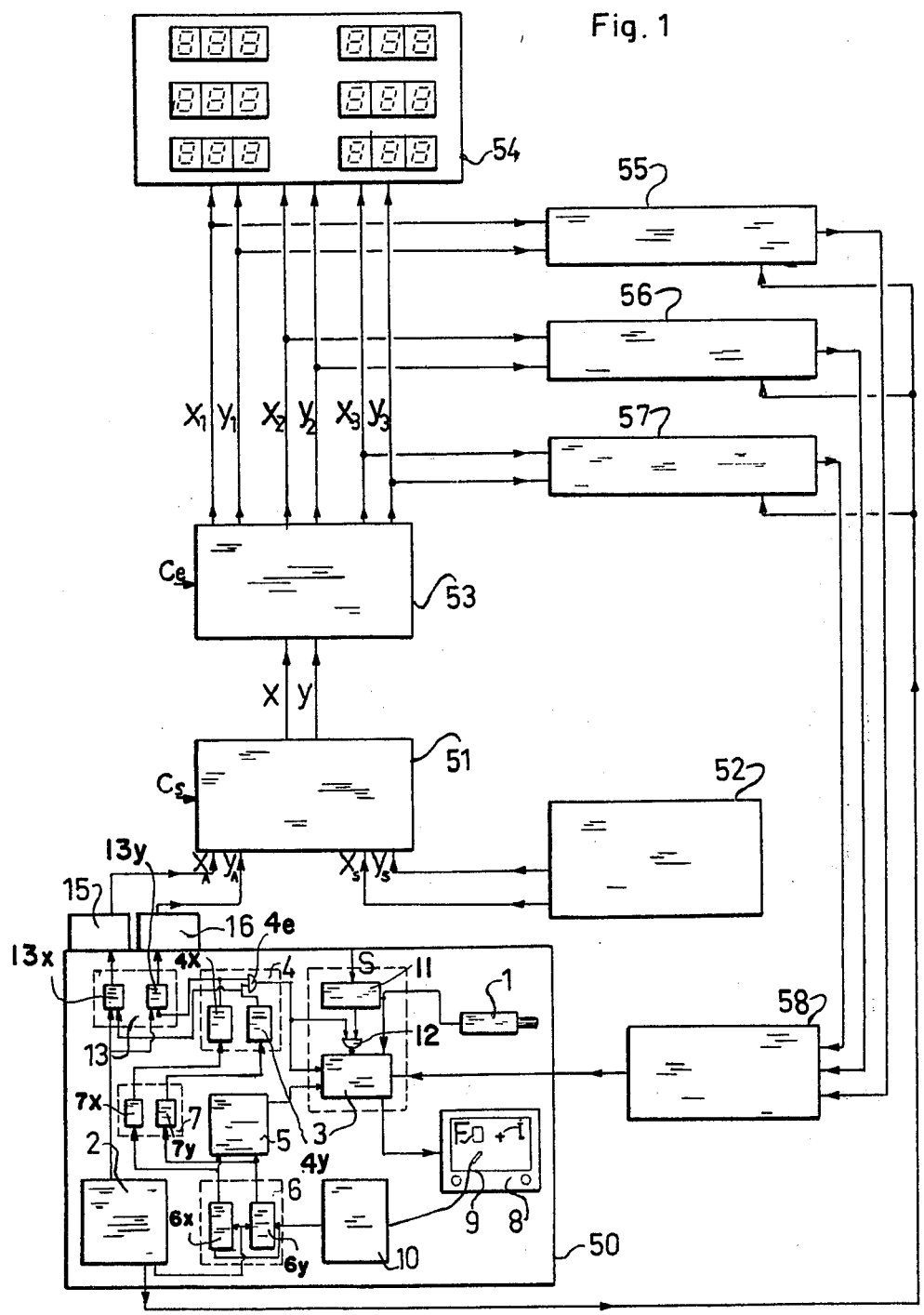
FIG. 1 shows a schematic diagram of one embodiment of the invention.

The device shown in FIG. 1 is intended to permit placement of a body in a reproducible manner in a position identical to a predetermined initial position. For example, this device can serve to position the head of a patient for a treatment with Gamma rays for treatment of a tumor. The first positioning is effected as a function of the radiograph tests, to direct the radiation to the concerned parts. It is necessary that the positioning be precisely the same in subsequent treatments.

The device of FIG. 1 comprises the device 50 for acquisition of the coordinates described in aforementioned Patent No. 75-18561 which is incorporated herein by reference. The device 50 comprises television camera 1 which is synchronized by the clock 2 which commands the electronic sweeping. The video signal delivered by the camera is injected into the video mixer 3 which also receives the index signals from the index generator 4 and the window signals from the window generator 5.

The index and window generators 4 and 5 ae unlatched by a window positioning circuit 6, the former by interposition of an unlatching index 7 and the latter directly.

The video mixer 3 effects mixing of the received signals and generates a composite video signal which is injected into the television monitor 8. Thus, there appear on the screen of this monitor 8 visualized images captured by the camera 1, and in superimposition, a window F and an index I.

Additionally, a photosensitive stylus 9 may be displaced along the screen of the monitor 8. This stylus comprises, in a conventional manner, a photo-diode at the end connected to a preamplifier for developing a signal characteristic of the luminance of the zone opposite which the stylus is placed.

The signal from the stylus is injected into a threshhold detector, of a well known type, which generates for each period an impulse corresponding to the first excess of the received threshhold signal which the detector detects. In the case where there is no excess, the detector does not furnish a signal, but in the other case, it furnishes a unique impulse. The control of the detector is accomplished in a manner such that the threshhold is at a slightly lower level than the maximum amplitude of the impulses corresponding to the lumination of the window F. It is pointed out that in a known manner, the control of the threshhold may be automatically indexed at this value such that variations in the lumination of the window do not affect the position of the impulse coming from the detector at each period.

The signal generated by the threshhold detector is injected into the window positioning circuit 6. This circuit comprises two similar oscillator assemblies 6x and 6y adapted to deliver two series of impulses out of phase respectively in line frequency and in sweep frequency from the impulse furnished by the threshhold detector.

The unlatching index circuit 7 receives the signals from the assemblies 6x and 6y. This circuit 7 comprises two similar delay circuit assemblies 7x and 7y adapted to deliver two series of out of phase impulses of a time constant delayed respectively in line and in sweep from the impulses received from the window positioning circuit 6.

The impulses from the unlatching index circuit 7 are received in the index generator 4 which comprises two similar assembly 4x and 4y, one adapted to furnish a line component and the other adapted to furnish a sweep component of the index signal. The intersection of these components define a punctual zone comprising the index. The intersection is accomplished in the AND gate 4p, and the corresponding signal is injected into the video mixer 3 to accomplish superimposition of the index on the monitor screen.

The video mixer is advantageously supplied with the signal in such a manner to insure maximum contrast with the image on which it is superimposed—in white when the image is dark and in black when the image is light. The decision is made by means including a manual control switch S, and further includes a threshhold detector 11 adapted to receive the video signal and compare it to a predetermined threshhold and deliver a logic signal characteristic of the value of the video signal compared to the threshhold.

A logic gate 12 is addressed by the logic signal from the threshhold detector 11 and by the index generator 4. The logic gate 12 is adapted to furnish the logical product of the signals it receives and is joined with the control entrance of the level of superimposition which the mixer 3 permits. The control S permits adjustment of the threshhold value.

Additionally, the apparatus includes a measuring assembly 13 which receives signals from the index generator and the clock in order to measure the time difference separating the arrival of the index signals and the reference signals. The assembly includes two logic triggers 13x and 13y for receiving respectively the line frequency reference and index signals and the sweep frequency reference and index signals. Each logic trigger furnishes an electrical impulses of a amplitude proportional to a coordinate (abscissa or ordinate) of the point in coincidence with the index.

The conversion blocks 15 and 16 receive the coordinate signals and convert them to a numeric code form.

Thus there are available at the output of the conversion blocks 15 and 16, situated before the measuring assembly 13, an abscussus signal and an ordinate signal in numeric code form. In the embodiment described, the coordinates coded in numeric form belong to an input set $X_a$, $Y_a$, of a selector 51 with manual control $C_s$, of digital type, adapted to store numerical inputs.

This selector has another group of inputs $X_s$, $Y_s$, which are connected to the outputs of a digital storage 52, adapted to store numerical inputs.

Control of selector 51 directs the signals from one or the other set of inputs toward its set of outputs X, Y.

The group of outputs of the selector is connected to the inputs of a digital buffer 53 which is adapted to contain the coordinates of three points coded in numeric form. An entry control $C_e$ loads these coordinates into the various cells of the storage.

This storage comprises three sets of outputs $X_1Y_1$, $X_2Y_2$, $X_3Y_3$, to which are respectively delivered the coordinates of the three stored points.

These sets of outputs are connected to viewer 54 to assure the display of the numeric coordinates coming from the buffer; in the example shown, these visualization means are constituted of 6 sets of exhibitors of seven segmented electroluminescent diodes.

Also, each set of outputs $X_1Y_1$, $X_2Y_2$, $X_3Y_3$ is connected to a digital synthesizer 55, 56 or 57, which receives the signals from the clock 2 and delivers to its output, at vision frequency, an impulse which is a function of the numeric coordinates received, the impulse characterizing the relevant point.

The impulses characterizing each of the three points are fed into a mixer 58 with logic or function. The impulses issued from mixer 58 are delivered to VIDEO mixer 3 to be added to the video signal and to generate three luminous zones of small dimensions corresponding to the three points by superimposition on the screen of monitor 8.

In the course of the first treatment, three distinct points are tatooed on the skin of the patient and the patient is placed in the suitable treatment position.

The control of the selector is placed in a such a manner that coordinates $X_A$, $Y_A$ are available to its outputs X, Y.

In the process explained in the application for the principal patent, the photosensitive marker 9 is displaced before the screen of the monitor to bring the index I to coincide with the image of one of the tatooed indentification points.

When the coincidence is obtained, the entry control $C_e$ is maneuvered by buffer 53 to store the coordinates of the index which correspond to the coordinates of the first reference point $X_1$, $Y_1$.

These coordinates are displayed on two of the sets of exhibitors of viewer 54.

The synthesizer 53 receives coordinates $X_1$, $Y_1$ from this point and delivers an impulse which causes the appearance of a synthetic point; this point is superimposed with the index and with reference point $X_1$, $Y_1$, since it has the same coordinates; it remains in place when the index is displaced.

The process of acquisition of the coordinates $X_2Y_2$, $X_3Y_3$ of the two other reference points is the same.

These visible coordinates on the exhibitors 54 are noted on the record of the patient.

At the beginning of each subsequent treatment, these coordinates are loaded successively into buffer 53, and the control $C_s$ of the selector 51 is placed in the corresponding position. The appearance at 54 of the coordinates permits control.

Three points corresponding to the three sets of coordinates are synthesized on the screen of the monitor and it suffices to displace the patient to bring the image of each reference point to coincide with the corresponding synthetic point on the screen.

FIG. 2 shows one embodiment of a synthesizer which comprises two assemblies 59 and 60, each connected to clock 2 and to buffer 53 to respectively receive the abscissus X and the ordinate Y of the point to be considered: these assemblies are connected at their output to an AND logic gate 61 which provides the logic product of the pulses received.

Each assembly 59 or 60 comprises a series of programmable counters 59a, 59b, 59c or 60a, 60b, 60c, arranged in series and effected on the one hand by the clock, on the deduction entries and on the loading entries L or T, and on the other hand, by the signals representing the abscissus X or the ordinate Y in coded form on the programming entries.

The chronogram of FIG. 3a shows the signal $H_1$ coming from the clock and constituted of a series of time reference pulses representing the elementary points on a sweep line.

The chronogram of FIG. 3b shows signal L coming from the clock and constituted of a series of time reference impulses being produced at the beginning of each line.

Under the action of each impulse L, the series of counters 59a, 59b, 59c is set at the value injected into its programming inputs, a value corresponding to the coded abscissus X.

Under the action of each impulse $H_1$, the state of the counters is decremented by one unit; when the counters of the series all pass to O state, the last one delivers an impulse $S_X$, of which the delay $T_X$ in relation to each beginning of line L is proportional to the abscissus X.

The function of assembly 60 is analogous. Signal $H_2$ which controls the decrement is shown in FIG. 3d; this signal is identical to signal L, but is shown in FIG. 3d in a different scale.

Signal T which controls the loading is shown in FIG. 3e. It comprises a series of time reference impulses which are produced at the beginning of each frame.

When counters 60a, 60b, 60c all reach 0, the last delivers an impulse $S_y$ of which the delay $T_y$ in relation to each beginning of frame T is proportional to the ordinate Y.

The impulses delivered by assemblies 59 and 60 at line frequency and at frame frequency thus present time gaps in relation to the beginnings of lines and at the beginning of frames which are proportional to the abscissa X and to the ordinate Y at the outputs of these assemblies. The AND gate 61 delivers an impulse each time that these impulses in X and in Y coincide in time, i.e., one impulse per frame. This impulse at frame frequency characterizes one point of the image and that is synthestized on the screen of the monitor.

Of course the invention is not limited to the preceding description but comprises all variations also. It can be applied in all cases where it is necessary to position an object or a body in space reproducibly.

While this invention has been described as having a preferred design, it will be understood that it is capable of further modification. This application, is therefore, intended to cover any variations, uses, or adaptations of the invention following the general principles thereof and including such departures from the present disclosure as come within known or customary practice in the art to which this invention pertains, and as may be applied to the essential features hereinbefore set forth and fall within the scope of this invention or the limits of the claims.

What is claimed is:

1. Device to permit positioning of an object or a body in space reproducibly, comprising:
   a television camera adapted to furnish a video signal corresponding to the object,
   a television monitor coupled to the camera to show the captured image,
   a synchronization clock adapted to furnish time reference signals particularly to control the electronic sweep of the camera,
   a photosensitive sensor, provided to be able to be displaced on the screen of the monitor and adapted to deliver a signal characteristic of the luminance of the zone opposite which it is placed,
   a threshold detector, connected to the photosensitive sensor to receive the signal furnished by the sensor and adapted to deliver an impulse when this signal exceeds a determined threshold,
   a frame positioning circuit, connected to the threshold detector and to the synchronization clock, and adapted to deliver a control signal, set off in relation to the received impulse at vision frequency in order to center a frame around the zone opposite which the photosensitive sensor is placed,
   a frame generator, connected to the positioning circuit and adapted to furnish a frame signal which can have two values, the one corresponding to a limited zone, called a frame, the other corresponding to zones outside the limited zone,
   a set-off index circuit, controlled by the frame positioning circuit and adapted to deliver a set-off signal in relation to the signal issued from the frame positioning circuit, at vision frequency, in order to position an index on the outside of the frame in constant position in relation to the frame,
   an index generator, connected to the set-off index circuit and adapted to furnish an index signal characterizing an image point,
   a video mixer connected to the camera and to the frame generator and to the aforementioned index generator, and this mixer is connected at its output to the television monitor to furnish it with a video signal representing the image of the plane on which are superimposed the frame and the index, and said video mixer is adapted to confer a predetermined luminance on said frame,
   a measuring assembly, connected to the index generator and to the clock to receive the signal issued from the index generator as well as the reference signals from the clock, and this assembly is adapted to measure the time separating the arrival of the index signals and reference signals, and said assembly furnishes signals characteristic of the position of the points in coincidence with the index,
   a manually controlled selector, having two sets of inputs and one set of outputs and adapted to connect, according to the state of its manual control, its set of outputs to one of the sets of inputs, and one of these sets of inputs is connected to the measuring assembly to receive the signals issuing from it,
   a storage which is adapted to store the coordinates of at least one point, and this storage has a set of outputs connected to the other set of inputs of the selector,
   a buffer which is adapted to store the coordinates of at least one point and having an entry control with manual release, and this storage is connected to the set of outputs from the selector and is provided with a set of outputs for each point to be stored,
   at least one point synthesizer receiving the clock signals and the signals from one set of outputs from the buffer and this synthesizer is adapted to deliver, at vision frequency, impulses characterizing the relevant point, and these impulses are received by the video mixer to be added to the video signal and to generate a superimposition on the monitor screen of at least one luminous zone of small dimensions.

2. Device as in claim 1, wherein the storage is a manual load storage associates with means for composition of the coordinates and adapted to be controlled by an operator.

3. Device as in claim 1, wherein the storage is an automatic load storage, of which the inputs are connected to the outputs of the buffer to receive the coordinates of each point from the buffer.

4. Device as in one of the claims 1, 2 or 3, comprising three point synthesizers, arranged in parallel and connected to three sets of outputs from the buffer and these synthesizers deliver impulses characterizing each of the points to the video mixer by means of a mixer with logic or function.

5. Device as in claim 4, wherein the buffer is associated with a viewer to assure the display of the coordinates coming from the buffer.

6. Device as in claim 5, wherein each point synthesizer comprises two assemblies of the same type connected to the clock and to the buffer to respectively receive the abscissa X and the ordinate Y of the point to be considered, and each assembly is adapted to deliver impulses respectively at line frequency and at frame frequency, of which the time gaps in relation to the signals from the clock from the beginning of lines or from beginnings of frames are proportional to the abscissa X or to the ordinate Y, and these assemblies are connected at their output to a logic and gate, effecting the logic product of the pulses at X and at Y.

7. Device as in claim 6, in which two conversion blocks are connected to the outputs of the measuring assembly and to the synchronization clock, the one to furnish an abscissa signal in numeric coded form, and the other to furnish an ordinate signal in numeric coded form, and wherein the selector, the buffer, the storage and each synthesizer are digital elements to treat inputs in numeric coded form.

8. Device as in claim 7 taken together, wherein each of the two assemblies of a point synthesizer comprises a series of programmable counters arranged in series and effected on the one hand by the clock signals on the decrement and loading inputs, and on the other hand by the signals representing the abscissa X or the ordinate Y in coded form on the programming inputs.

9. Process of positioning an object or a body in the space, to permit return of this object or body in a precisely reproducible position, wherein it consists of identifying three characteristic points of this object or body, putting the device to work as in Claim 4 in two phases, the one corresponding to the acquisition of the coordinates of the three points, and the other to the synthesis of these points and to the positioning of the object or the body, and the acquisition phase consists of the following:

aiming the camera on the object or the body to form an image thereof on the screen of the monitor, bringing the index into coincidence with one of the reference points by displacement of the photosensitive sensor, controlling the entry of the coordinates of the index in the buffer, the selector being in the position which assures the liaison between this buffer and the measuring element, repeating the operations for the other two of said reference points and transferring the coordinates of the three points into the storage, and the synthesis phase of the points and the positioning of the object or the body is as follows:

controlling the selector to transfer the contents of the storage into the buffer, and displacing the object or the body to bring the image of its characteristic points on the monitor screen to coincide with the synthesized points on the screen.

10. A device enabling positioning of an object in space reproducibly, comprising:

a television camera for furnishing a video signal corresponding to the object, a television monitor coupled to the camera for displaying the captured image, a synchronization clock adapted for furnishing time reference signals for controlling the electronic sweep of the camera, a photosensitive sensor, adapted to be displaced on the screen of said monitor and adapted to deliver a first signal characteristic of the luminance of the zone opposite which it is placed, a threshold detector, connected to said sensor for receiving said first signal and adapted to deliver an impulse when said first signal exceeds a determined threshold, a frame positioning circuit, connected to said threshold detector and synchronization clock, and adapted to deliver a second control signal, set off in relation to the received impulse at vision frequency in order to center a frame around the zone opposite which said photosensitive sensor is placed, a frame generator, connected to said positioning circuit and adapted to furnish a third frame signal having one of two values, one corresponding to a limited frame zone, the other corresponding to zones outside the limited frame zone, a set-off index circuit, controlled by said frame positioning circuit and for delivering a fourth set-off signal in relation to the signal issued from the frame positioning circuit, at vision frequency, for positioning an index on the outside of the frame zone in constant position in relation to the fre zone, an index generator connected to said set-off index circuit for furnishing a fifth index signal characterizing an image point, a video mixer connected to said camera. said frame generator and said index generator, and being connected at its output to said television monitor for furnishing it with a sixth video signal representing the image of the plane on which are superimposed said frame zone and the image point from said fifth signal, said video mixer being adapted to confer a predetermined luminance on said frame, a measuring assembly, connected to said index generator and to said clock for receiving said fifth signal amd said time reference signals from said clock, said measuring assembly being adapted to measure the time separating the arrival of said fifth signals and said time reference signals, and furnish sixth signals characteristic of the position of the points in coincidence with said index, a manually controlled selector, having two sets of inputs and one set of outputs and adapted to connect, according to the state of its manual control, said set of outputs to one of said sets of inputs, one of said sets of inputs being connected to said measuring assembly for receiving said sixth signals, a storage adapted to store the coordinates of at least one point, said storage having a set of outputs connected to the other set of inputs of said selector, a buffer for storing the coordinates of at least one point and having an entry control with manual release, said storage being connected to the set of outputs from the selector and provided with a set of outputs for each point to be stored, at least one point synthesizer receiving said time reference signals and the signals from one set of outputs from the buffer, said synthesizer being adapted to deliver, at vision frequency, inpulses characterizing the relevant point, and said impulses are received by the video mixed to be added to the video signal and to generate a superimposition on the monitor screen of at least one luminous zone of small dimensions.

* * * * *